US009582894B2

(12) United States Patent
Aalto-Setala et al.

(10) Patent No.: US 9,582,894 B2
(45) Date of Patent: Feb. 28, 2017

(54) VISUAL CARDIOMYOCYTE ANALYSIS

(71) Applicants: TAMPEREEN YLIOPISTO, Tampereen Yliopisto (FI); TTY-saatio, Tampere (FI)

(72) Inventors: Katriina Aalto-Setala, Tampere (FI); Anna Kiviaho, Tampere (FI); Jari Hyttinen, Tampere (FI); Antti Ahola, Tampere (FI); Markus Honkanen, Tampere (FI); Henna Venalainen, Nokia (FI)

(73) Assignees: TAMPEREEN YLIPOISTO, Tampereen Yliopisto (FI); TTY-SAATIO, Tampere (FI)

(*) Notice: Subject to any disclaimer, the term of this patent is extended or adjusted under 35 U.S.C. 154(b) by 0 days.

(21) Appl. No.: 14/651,532

(22) PCT Filed: Sep. 19, 2013

(86) PCT No.: PCT/FI2013/050905
§ 371 (c)(1),
(2) Date: Jun. 11, 2015

(87) PCT Pub. No.: WO2014/102449
PCT Pub. Date: Jul. 3, 2014

(65) Prior Publication Data
US 2015/0332477 A1    Nov. 19, 2015

(30) Foreign Application Priority Data

Dec. 27, 2012  (FI) .................................. 20126384

(51) Int. Cl.
G06K 9/00    (2006.01)
G06T 7/20    (2006.01)
(Continued)

(52) U.S. Cl.
CPC ....... *G06T 7/2033* (2013.01); *G01N 33/4833* (2013.01); *G06T 7/0016* (2013.01);
(Continued)

(58) Field of Classification Search
None
See application file for complete search history.

(56) References Cited

U.S. PATENT DOCUMENTS 8,582,823 B2 *  11/2013  Kunihiro ............... G06T 7/0016
                                                        382/106
9,053,352 B2 *  6/2015  Trumbull ........... G01N 15/1475
(Continued)

FOREIGN PATENT DOCUMENTS

WO    2008149055 A1    12/2008
WO    2011/122200 A1   10/2011
WO    2013/165301 A1   11/2013

OTHER PUBLICATIONS

Shapira-Schweitzer K et al.: Photopolymerizable hydrogel for 3-D culture of human embryonic stem cell-derived cardiomyocytes and rat neonatal cardiac cells, Journal of Molecular and Cellular Cardiology, Academic Press, GB, vol. 46, No. 2, Feb. 1, 2009 (Feb. 1, 2009), pp. 213-224, XP025770834, ISSN: 0022-2828, DOI: 10.1016/J.YJMCC.2008.10.018 [retrieved on Nov. 5, 2008] abstract, sections 2, 3 figures 3, 5-7.
(Continued)

Primary Examiner — Nancy Bitar
(74) Attorney, Agent, or Firm — Young & Thompson

(57) ABSTRACT

Method for analyzing the beating of a derived human cardiomyocyte (CM) includes obtaining the derived human CM, capturing a sequence of images depicting the derived human CM over an analysis period, and determining at least one signal descriptive of the beating of the derived human CM during the analysis period on basis of the sequence of captured images. Apparatuses, and a computer program for
(Continued)

analyzing the beating of a derived human CM are configured to obtain: the sequence of images depicting the derived human CM over an analysis period, information indicative of the region of the images depicting the derived human CM, information indicative of two or more sub-regions within the region, and determine two or more signals characterizing the displacement within the region of images depicting the derived human cardiomyocyte, each signal characterizing the extent of displacement within a respective sub-region of the region as a function of time.

18 Claims, 9 Drawing Sheets

(51) Int. Cl.
    *G01N 33/483*     (2006.01)
    *G06T 7/00*     (2006.01)

(52) U.S. Cl.
    CPC .......... *G06T 7/0081* (2013.01); *G06T 7/2013* (2013.01); *G06T 2207/10016* (2013.01); *G06T 2207/10056* (2013.01); *G06T 2207/20021* (2013.01); *G06T 2207/30024* (2013.01); *G06T 2207/30048* (2013.01)

(56) References Cited

U.S. PATENT DOCUMENTS

2006/0275745 A1* 12/2006 Schwarz .............. G06K 9/0014
                                                                   435/4
2013/0070971 A1     3/2013 Kunihiro et al.

OTHER PUBLICATIONS

Tomohiro Hayakawa et al.: "Noninvasive Evaluation of Contractile Behavior of Cardiomyocyte Monolayers Based on Motion Vector Analysis", Tissue Engineering Part C: Methods, vol. 18, No. 1, Jan. 1, 2012 (Jan. 1, 2012), pp. 21-32, XP055093305, ISSN: 1937-3384, DOI: 10.1089/ten.tec.2011.0273 abstract sections "Introduction", "Materials and Methods", "Results" A figures 1, 4.

Anonymous: "Cardiomyocyte Beating Assay", Jan. 1, 2011 (Jan. 1, 2011), pp. 1-6, XP055093303, Retrieved from the Internet: URL:http://www.predictivebio.com/PB/cardio myocyte beating assay.html retrieved on Dec. 13, 2013] the whole document.

Xiaofeng Liu et al: "Motion-Based Segmentation for Cardiomyocyte Characterization", Oct. 1, 2012 (Oct. 1, 2012), Spatio-Temporal Image Analysis for Longitudinal and Time-Series Image Data, Springer Berlin Heidelberg, Berlin, Heidelberg, pp. 137-146, XP047017812, ISBN: 978-3-642-33554-9 abstract section 2.1.

International Search Report, dated Jan. 2, 2014, from corresponding PCT application.

FI Search Report, dated Aug. 26, 2013, from corresponding FI application.

Written Opinion, dated Jun. 20, 2014, from corresponding PCT application.

\* cited by examiner

300

US 9,582,894 B2

VISUAL CARDIOMYOCYTE ANALYSIS

FIELD OF THE INVENTION

The present invention relates to analysis of functionality human cardiomyocyte (CM). In particular, the present invention relates to a method, to an apparatus, to a computer program and use thereof for analyzing functionality of one or more human CMs.

BACKGROUND

Genetic disorders having cardiac effects are, typically, potentially lethal without proper therapy or medication, and therefore it is of essential importance to detect signs of such a disorder early on. Moreover, cardiac side effects are a one of the most common reason for withdrawal of a drug from the market, and therefore reliably capturing any potential cardiac side effects of a drug already during the development phase would be highly beneficial.

Cardiac safety analyses are typically carried out using animals as model organisms and/or ectopic expression of single ion channels in non-cardiac human cells. Human cardiomyocytes (CMs) have been very challenging to study, since primary CMs are hard to obtain as the myocardial biopsy is a high risk procedure and the CMs dedifferentiate fast and stop beating in cell culture conditions. Moreover, previously known techniques for measuring the functionality of the CMs are challenging and do not provide high or even medium throughput.

While cardiac effects can in principle be examined by analyzing the functionality of human CMs, known techniques for such analysis are typically time-consuming and also somewhat unreliable or even impractical to properly support diagnostic purposes, hence failing to provide an analysis of the functionality of CMs that would provide a satisfactory basis for wide-spread use for supporting diagnostic purposes. In this regard, e.g. "Brüggemann A., S. Stoelzle, M. George, J. C. Behrends, and N. Fertig, Microchip technology for automated and parallel patch-clamp recording, Small 2:840-846, 2006" discloses so-called patch clamp approach that may be used to analyze the functionality of a single CM. However this technique requires special, relatively expensive instrumentation, and laborious manual work requiring highly skilled personnel. For example "Braeken D., R. Huys, D. Jans, J. Loo, S. Severi, F. Vleugels, G. Borghs, G. Callewaert, and C. Bartic, Local electrical stimulation of single adherent cells using three-dimensional electrode arrays with small interelectrode distances. Conf. Proc. IEEE Eng, Med. Biol. Soc. 2756-2759, 2009" and "Pekkanen-Mattila M., E. Kerkelä, J. M. A. Tanskanen, M. Pietilä, M. Pelto-Huikko, J. Hyttinen, H. Skottman, R. Suuronen, and K. Aalto-Setälä, Substantial variation in the cardiac differentiation of human embryonic stem cell lines derived and propagated under the same conditions—a comparison of multiple cell lines, Ann. Med. 41:360-370, 2009" disclose a technique based on microelectrode arrays (MAE) that provide a platform for analyzing larger aggregates of CMs with less manual work than required in the patch clamp technique, but due to dimensions of the electrodes and distances between electrodes, they are not suited for studying a single CM. As further example of related art, "Novakova M., J. Bardonova, I. Provaznik, E. Taborska, H. Bochorakova, H. Paulova, and D. Horky, Effects of voltage sensitive dye di-4-ANEPPS on guinea pig and rabbit myocardium, Gen. Physiol, Biophys. 27:45-54, 2008" discloses a technique based on voltage sensitive dyes such as e.g. di-8-ANNEPS that provides a solution to analyze a single CM. However, this technique is based on fluorescence imaging and the dyes interact with some ion channels e.g. hERG, thus potentially altering the electrophysiological properties of the CMs.

SUMMARY

Therefore, it is an object of the present invention to provide a technique for analysis of human CMs that is reliable, straightforward to apply and enables prolonged follow-up of the CMs. Moreover, it is a further object of the present invention to provide a technique enables analysis of a single human CM.

The objects of the invention are reached by a method, by an apparatus and by a computer program as defined by the respective independent claims.

In this regard, a novel method for analyzing the beating of a derived human cardiomyocyte is provided. Said method comprises obtaining the derived human cardiomyocyte, capturing a sequence of images depicting the derived human cardiomyocyte over an analysis period, and determining at least one signal descriptive of the beating of the derived human cardiomyocyte during the analysis period on basis of the sequence of captured images.

Further in this regard, a novel apparatus for analyzing the beating of a derived human cardiomyocyte on basis of a sequence of captured images is provided. Said apparatus comprises an image acquisition portion configured to obtain the sequence of images depicting the derived human cardiomyocyte over an analysis period, an analysis focusing portion configured to obtain information indicative of the region of the images depicting the derived human cardiomyocyte, and to obtain information indicative of two or more sub-regions within said region and an image analysis portion configured to determine two or more signals characterizing the displacement within said region of the images depicting the derived human cardiomyocyte, each signal characterizing the extent of displacement within a respective sub-region of said region as a function of time.

Further in this regard, a second novel apparatus for analyzing the beating of a derived human cardiomyocyte on basis of a sequence of captured images is provided. Said apparatus comprises at least one processor and at least one memory including computer program code for one or more programs, the at least one memory and the computer program code configured to, with the at least one processor, cause the apparatus at least to obtain the sequence of images depicting the derived human cardiomyocyte over an analysis period, to obtain information indicative of the region of the images depicting the derived human cardiomyocyte, to obtain information indicative of two or more sub-regions within said region, and to determine two or more signals characterizing the displacement within said region of the images depicting the derived human cardiomyocyte, each signal characterizing the extent of displacement within a respective sub-region of said region as a function of time.

Further in this regard, a novel computer program for analyzing the beating of a derived human cardiomyocyte on basis of a sequence of captured images is provided. The computer program comprises one or more sequences of one or more instructions which, when executed by one or more processors, cause an apparatus at least to obtain the sequence of images depicting the derived human cardiomyocyte over an analysis period, to obtain information indicative of the region of the images depicting the derived human cardiomyocyte, to obtain information indicative of two or more sub-regions within said region, and to determine two or more signals characterizing the displacement within said region of the images depicting the derived human cardiomyocyte, each signal characterizing the extent of displacement within a respective sub-region of said region as a function of time.

The computer program may be embodied on a volatile or a non-volatile computer-readable record medium, for example as a computer program product comprising at least one computer readable non-transitory medium having program code stored thereon, the program code, which when executed by an apparatus, causes the apparatus at least to perform the operations described hereinbefore for the computer program.

The exemplifying embodiments of the invention presented in this patent application are not to be interpreted to pose limitations to the applicability of the appended claims. The verb "to comprise" and its derivatives are used in this patent application as an open limitation that does not exclude the existence of also unrecited features. The features described hereinafter are mutually freely combinable unless explicitly stated otherwise.

The novel features which are considered as characteristic of the invention are set forth in particular in the appended claims. The invention itself, however, both as to its construction and its method of operation, together with additional objects and advantages thereof, will be best understood from the following detailed description of specific embodiments when read in connection with the accompanying drawings.

DETAILED DESCRIPTION OF SOME EMBODIMENTS

Figure 1:
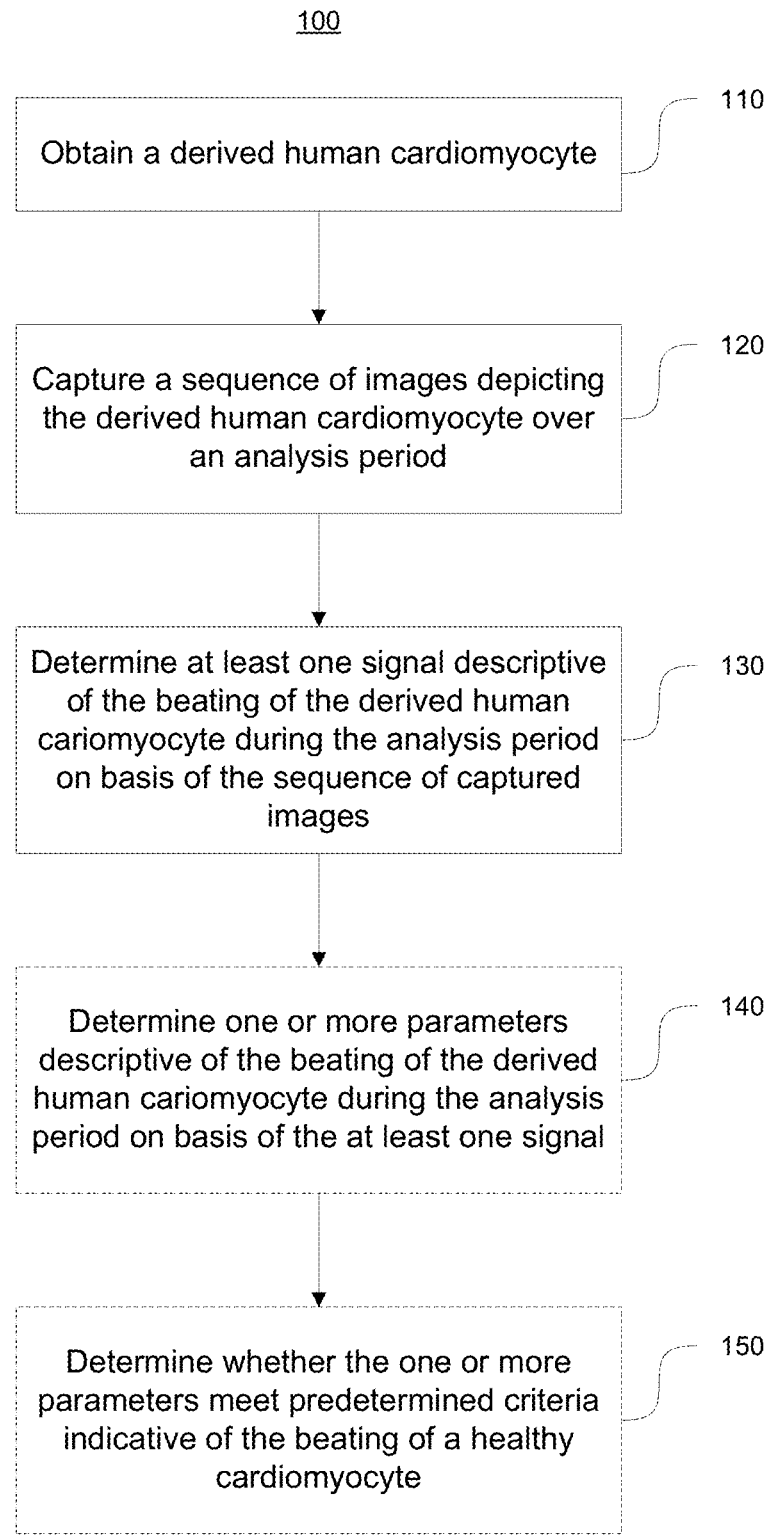
FIG. 1 illustrates a method in accordance with an exemplifying embodiment of the present invention.

Recently developed techniques to reprogram human cells provide interesting possibilities to study differentiated human cells, which have not been available before due to too risky procedure or due to rapid dedifferentiation of the primary cells in culture. Such techniques provide, for example, interesting possibilities to study human cells, for example human cardiomyocytes (CMs).

As an example in this regard, recent developments in stem cell technology, namely invention of induced pluripotent stem (iPS) cells, has paved the way for techniques characterizing both the iPS cells themselves and cells derived from iPS cells. Pluripotent human stem cells, opposite to other primary human cells, are capable to proliferate and renew themselves, at least in theory, indefinitely or alternatively differentiate into any cell type of human body. iPS cells can be obtained from any individual, also from those carrying certain genotype, by reprogramming already differentiated adult cells, such as skin fibroblasts, into a pluripotent state. Such iPS cells can then be differentiated into the cell type of interest and with disease and genotype specific iPS cells to obtain differentiated cells, for example to CMs that carry the disease causing phenotype. In this regard, it has been shown that the genotype and phenotype of the cells so derived is similar to that of the actual cells of the individual, e.g. the iPS derived CMs may carry the same mutation as the CMs in the heart of the individual, see e.g. Lahti A. L., V. J. Kujala, H. Chapman, A. P. Koivisto, M. Pekkanen-Mattila, E. Kerkelä, J. Hyttinen, K. Kontula, H. Swan, B. R. Conklin, S. Yamanaka, O. Silvennoinen, and K. Aalto-Setälä, Model for long QT syndrome type 2 using human iPS cells demonstrates arrhythmogenic characteristics in cell culture, Dis. Model. Mech. 5:220-230, 2012.

As another example, differentiated cells can also be obtained by so called direct differentiation method. This method enables the induction of differentiated cells, e.g. CMs, directly from another differentiated cell type, e.g. from fibroblast, thus bypassing the stem cell state applied in the iPS approach described hereinbefore.

In the following, the term derived human CM is used to refer to a CM derived from a human cell of different from a CM e.g. by using the iPS method or the direct differentiation method referred to hereinbefore. The cell of other type used as basis for deriving the human CM is referred to in the following as a source cell. Non-limiting examples of suitable types of source cells with straightforward access include dermal fibroblasts or keratinocytes, blood cells such as leucocytes, mucosal cells and endothelial cells. Derived human CMs provide interesting possibilities for non-invasive study of individual CMs to enable analysis of its beating behavior and, in particular, any deviations from beating behavior of a healthy human CM. Consequently, results of such analysis are potentially useable, for example, in detection of genetic disorders having a cardiac effect and/or in detection of cardiac side effects of a drug during development or testing of the drug.

In the following, a method for analyzing the beating of one or more derived human CMs is described. The method proceeds from the novel observation that at least some of the human CMs derived on basis of a source cell originating from a person suffering from genetic disorder resulting in cardiac effects exhibit beating behavior that is different from the beating behavior of a healthy CM. Similarly, human CMs derived on basis of a source cell originating from a healthy reference person but which have been exposed to a substance of interest, e.g. to a drug or to a molecule, that results in cardiac effects during or after the derivation phase exhibit beating behavior that is different from the beating behavior of a healthy CM. One advantage of the analysis method, described in detail hereinafter, is that it provides a non-invasive and label free technique for analyzing the beating behavior of one or more human CMs. Moreover, as a further advantage, this analysis method enables a study of the behavior of one or more human CMs over a prolonged period of time. A yet further advantage of this analysis method is that is enables analysis of a single human CM, thereby providing indication of the beating behavior that is independent of the beating behavior of adjacent human CMs and hence also provides basis for high throughput analysis of human CMs. Furthermore, yet another advantage of this analysis method is the possibility to analyze the cardiac effect of repeated and/or prolonged exposure to a substance of interest.

Therefore, the present invention proposes a method for analyzing the beating of a derived human CM. As a non-limiting example, a method 100 is illustrated by a flowchart in FIG. 1. The method 100 comprises obtaining induced derived human CM, as indicated in block 110, capturing a sequence of images depicting the derived human CM over an analysis period, as indicated in block 120, and determining at least one signal descriptive of the beating of the derived human CM during the analysis period on basis of the sequence of captured images, as indicated in block 130. The method 100 may further comprise determining one or more parameters descriptive of the beating of the derived human CM on basis of the at least one signal, as indicated in block 140. The method 100 may further comprise determining whether the one or more parameters meet predetermined criteria indicative of the beating of a healthy human CM, as indicated in step 150. Non-limiting examples describing the method 100 in more detail are provided hereinafter.

Advantageously, the method 100 is applied for analyzing the beating of a single dissociated derived human CM or a plurality (i.e. two or more) of derived dissociated human CMs. A benefit of analyzing a single dissociated derived human CM is that the CM under investigation is not influenced by any neighboring CMs (or by cells of other type) and hence the reliability and accuracy of the analysis can be improved.

The beating of a human CM, an induced or a primary one, exhibits periodically alternating periods of contraction and relaxation at a rate characteristics thereto under the circumstances. The beating may be considered to consist of a sequence of beating cycles, a cycle i having the duration T(i), the cycle i comprising a period of contraction having duration $T_c(i)$ and a period of relaxation having duration $T_r(i)$. The period of contraction may be further divided into a period of contractile movement having duration $T_{cM}(i)$ and a period of the human CM being in (fully) contracted state having duration $T_{cS}(i)$ and, likewise, the period of relaxation may be further divided into a period of relaxation movement having duration $T_{rM}(i)$ and a period of the human CM being in a relaxed state having duration $T_{rS}(i)$. It is possible to further divide the period of contraction and/or the period of relaxation into further transition periods between the periods or states referred hereinbefore.

Figure 2A:
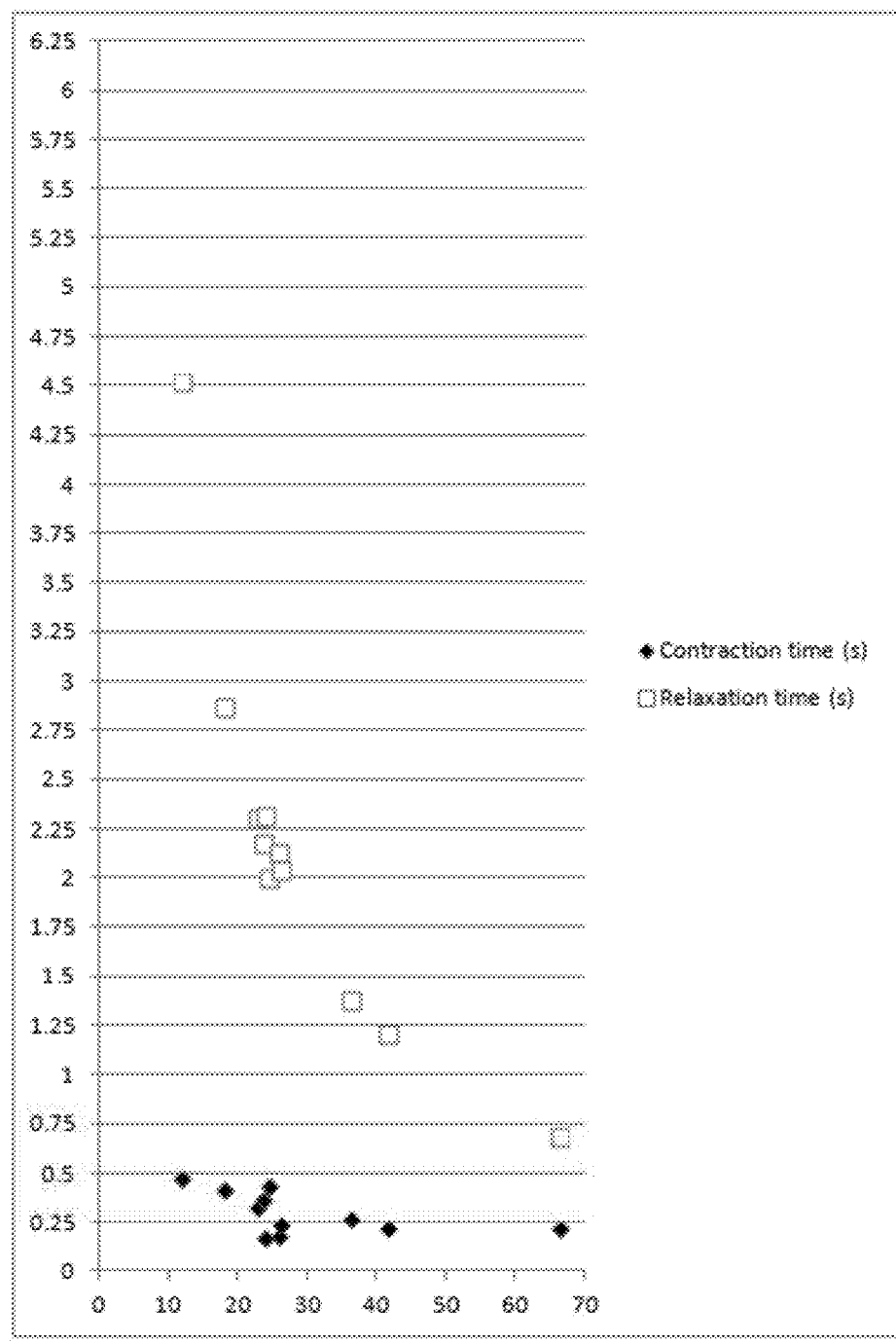
FIG. 2a illustrates examples of the duration of the period of contraction in relation to the beating rate and the duration of the period of relaxation in relation to the beating rate for a healthy human CM
Figure 3A:
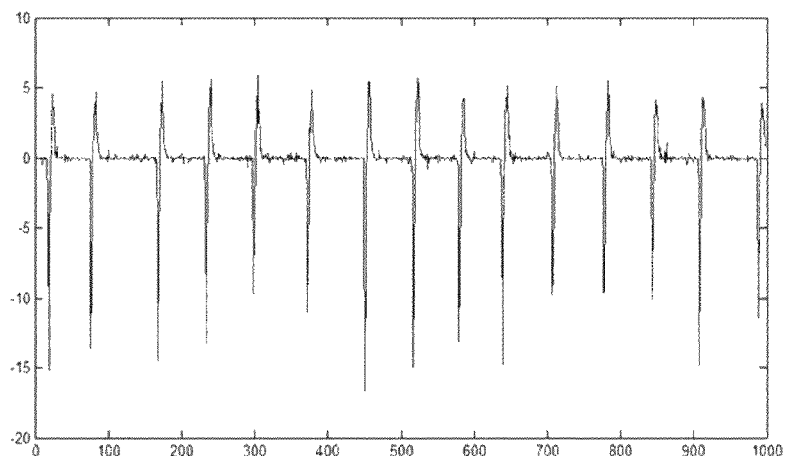
FIG. 3a illustrates an example of a signal descriptive of the beating of a healthy human CM as a function of time.

In case of a healthy human CM, although the durations of the cycles T(i) may exhibit some variation over time even in static or relatively static circumstances and correlation with beating rate, the duration of the period of contraction $T_c(i)$ is typically under 500 milliseconds and correlates to a similar extent with the beating rate. FIG. 2a illustrates examples of the duration of the period of contraction $T_c(i)$ in relation to the beating rate (indicated as diamonds) and the duration of the period of relaxation $T_r(i)$ in relation to the beating rate (indicated as squares) for a healthy human CM. As can be seen in FIG. 2a, the duration of the period of relaxation $T_r(i)$ varies significantly more with the beating rate than the duration of the period of contraction $T_c(i)$. Moreover, for a healthy human CM a period of contraction is typically completely or almost completely covered by the period of contractile movement and hence the period of relaxation movement following a given period of contractile movement typically starts without a significant period of fully contracted state therebetween. This is further illustrated in FIG. 3a providing an example of a signal descriptive of the beating of a healthy human CM as a function of time. In FIG. 3a, signal extending downwards from the approximate baseline indicates contractile movement, signal extending upwards form the approximate baseline indicates relaxation movement, and signal at the approximate baseline indicates either fully contracted state between a period of contractile movement and the following period of relaxation movement or fully relaxed state between a period of relaxation movement and the following period of contractile movement.

Figure 2B:
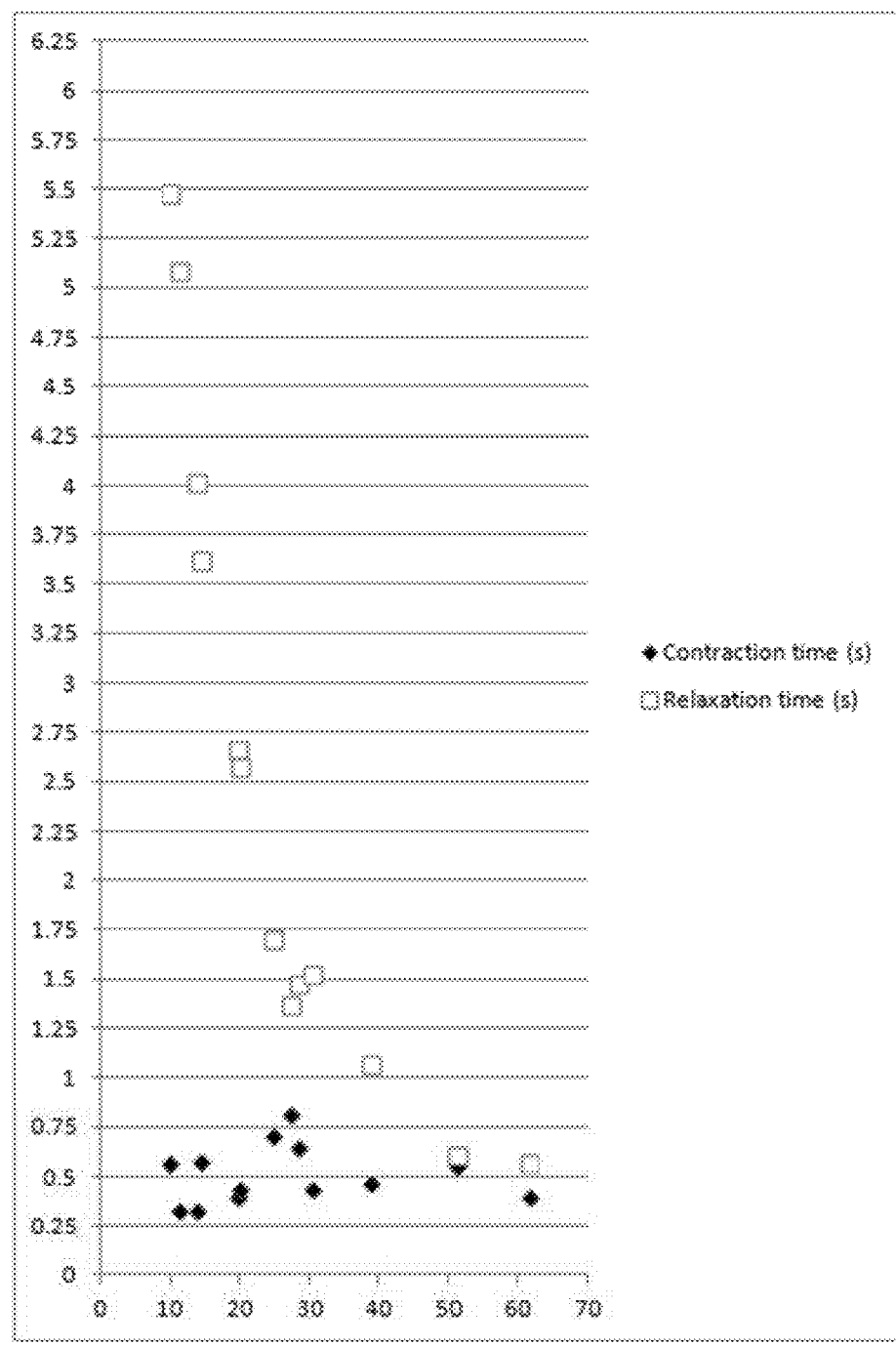
FIG. 2b illustrates examples of the duration of the period of contraction in relation to the beating rate and the duration of the period of relaxation in relation to the beating rate for an unhealthy human CM
Figure 3B:
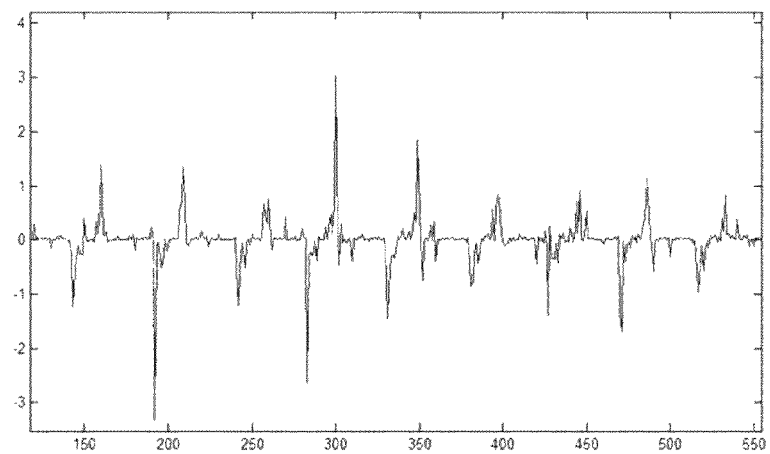
FIG. 3b illustrates an example of a signal descriptive of the beating of an unhealthy human CM as a function of time.
Figure 3C:
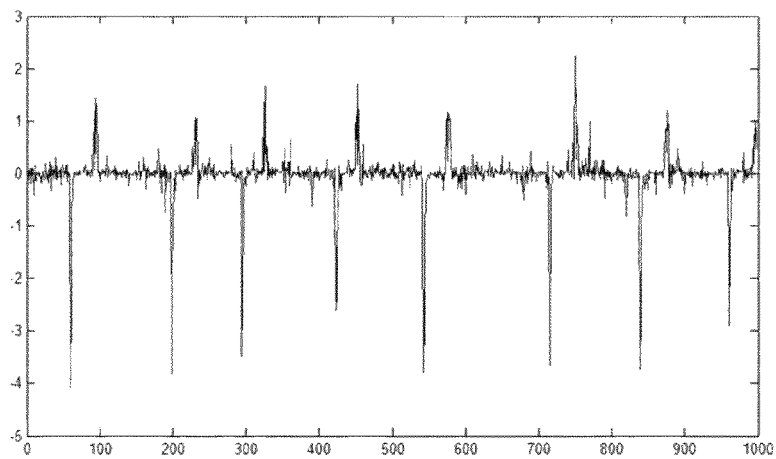
FIG. 3c illustrates an example of a signal descriptive of the beating of a human CM exposed to a substance of interest.

In contrast, for an unhealthy human CM, e.g. for one suffering from abnormal cardiac function e.g. due to genetic disorder or due to exposure to a drug, for example the duration of a period of contractile movement $T_{cM}(i)$ and/or the duration of a period of relaxation movement $T_{rM}(i)$ may be shortened or prolonged compared to those of a healthy human CM, In this regard, FIG. 2b provides examples of the duration of the period of contraction $T_c(i)$ in relation to the beating rate (indicated as diamonds) and the duration of the period of relaxation $T_r(i)$ in relation to the beating rate (indicated as squares) for an unhealthy human CM. As can be seen in the examples of FIG. 2b, especially the duration of the period of relaxation $T_r(i)$ in relation to the beating rate exhibits a rather clear difference to that of healthy human CMs. This phenomenon may be visible in all beating cycles or at least in some of the beating cycles of an unhealthy human CM. Further in this regard, FIG. 3b provides an example of a signal descriptive of the beating of an unhealthy human CM as a function of time. As the example of FIG. 3b indicates, e.g. a human CM carrying a gene mutation is likely to exhibit periods of contraction consisting both a period of contractile movement and a clearly identifiable period of fully contracted state or a period of disrupted relaxation movement between the period of contractile movement and the following period of (normal) relaxation movement. Along similar lines, alterations in duration of period of fully contracted state and characteristics of the relaxation movement can also be observed in human CMs where a substance of interest, e.g. a drug, a molecule or a toxin, affects the cardiac functionality, as illustrated in FIG. 3c by an exemplifying signal descriptive of the beating of a human CM exposed to a substance of interest. Conversely, the duration of a period of the human CM being in (fully) contracted state $T_{cS}(i)$ exceeding that considered to indicate a healthy human CM and/or the duration of a period of the human CM being in a relaxed state $T_{rS}(i)$ falling short of a threshold value considered to indicate a healthy human CM may be likewise considered as indications of an unhealthy human CM.

Consequently, the one or more parameters descriptive of beating of the derived human CM may comprise, for example, parameters descriptive of one or more of the duration of the cycle $T(i)$, duration of the contraction period $T_c(i)$, duration of the relaxation period $T_r(i)$, duration of the period of contractile movement $T_{cM}(i)$, duration of the period of the human CM being in (fully) contracted state $T_{cS}(i)$, duration of the period of relaxation movement $T_{rM}(i)$ and duration of the period of the human CM being in a relaxed state $T_{rS}(i)$. Each of these exemplifying parameters may be indicate the absolute value of the respective parameter or its value in relation of the corresponding beating rate of the human CM. Alternatively or additionally, the one or more parameters descriptive of beating of the derived human CM may comprise any parameter derived from the parameters descriptive of the duration of the cycle, (sub-)periods thereof and/or transition periods therebetween, for example one or more of duration of the period of contraction in relation to the duration of the cycle $T_c(i)/T(i)$, duration of the relaxation period in relation to the duration of the cycle $T_r(i)/T(i)$, duration of the period of contractile movement in relation to the duration of the cycle $T_{cM}(i)/T(i)$, duration of the period of the human CM being in (fully) contracted state in relation to the duration of the cycle $T_{cS}(i)/T(i)$, duration of the period of relaxation movement in relation to the duration of the cycle $T_{rM}(i)/T(i)$, duration of the period of the human CM being in a relaxed state in relation to the duration of the cycle $T_{rS}(i)/T(i)$, duration of the contraction period in relation to the duration of the relaxation period cycle $T_c(i)/T_r(i)$ and duration of the period of contractile movement in relation to the duration of the period of relaxation movement $T_{cM}(i)/T_{rM}(i)$, duration of the period of contractile movement in relation to the duration of the period of contraction $T_{cM}(i)/T_c(i)$ and duration of the period of relaxation movement in relation to the duration of the period of relaxation $T_{rM}(i)/T_r(i)$. Such parameters may be determined e.g. individually for a number cycles i in a range of interest $i=i_1$ to $i_2$ or as the average values of the durations or parameters derived therefrom in the range of interest.

As described hereinbefore, the derived human CM may be obtained by differentiating the CM by reprogramming a cell differentiated into pluripotent stem cell (iPS cell) or by directly reprogramming any differentiated cell into a CM. The primary source cell may be any human cell, e.g. a dermal fibroblast, a keratinocyte, a blood cell such as a leucocyte, a mucosal cell or an endothelial cell. The exact process of establishing the one or more iPS cells or iPS cell lines, exact characteristics of the iPS cells and the exact process of differentiating/culturing a derived human CM on basis of an iPS cell or a source cell of other type are outside the scope of the present invention and any suitable process known in the art may be employed.

One or more dissociated derived human CM(s) may be obtained from one or more differentiated clusters of derived human CMs. In such a scenario, obtaining the derived human CM(s) may comprise dissociating one or more derived human CMs from the differentiated clusters before further analysis in order to produce dissociated CM(s) that are not attached to each other and thereby not directly influenced by neighboring cells.

According to an embodiment, beating aggregates are first isolated from the cluster(s) using a cutting tool such as a micro scalpel, collected, and treated with an enzyme, e.g. collagenase A. Subsequently, the collected aggregates are re-suspended e.g. by flushing up and down to break up the cell clusters into dissociated derived human CMs. The derived dissociated human CMs are then allowed to attach onto cell culture well plates. Subsequently, the sequence of images depicting the derived dissociated human CM(s) may be obtained, as will be described in detail in the following.

The derived CM to be analyzed may be derived e.g. on basis of a source cell originating from an individual who is suspected to carry a genetic disorder or to suffer from other condition that may have cardiac effects resulting in irregular or abnormal beating behavior of the CMs. Consequently, the subsequent analysis of such derived human CMs indicating irregular or abnormal beating behavior may be considered as an indication of existence of such genetic disorder or other condition and/or the extent thereof. Alternatively, as a second example, the derived CMs to be analyzed may be derived e.g. on basis of a source cell originating from a healthy individual and subsequently exposed to a substance of interest, e.g. a drug, a molecule or a toxin under development or testing. Consequently, the subsequent analysis of such derived human CMs indicating irregular or abnormal behavior may be considered as an indication of the substance of interest potentially having cardiac side-effects and/or the extent thereof. As a third example, the derived CM to be analyzed may be derived e.g. on basis of a source cell originating from an individual who is known to carry a genetic disorder or to suffer from other condition that may have cardiac effects resulting in irregular or abnormal beating behavior of the CMs and subsequently exposed to a substance of interest under development or testing. Consequently, the subsequent analysis of such derived human CMs indicating healthy behavior may be considered as an indication of the substance of interest potentially having an effect of mitigating the cardiac effect due to the genetic disorder or the other condition and/or the extent thereof. Instead of applying a substance of interest in the second and third examples discussed herein, the derived CM under study may be e.g. exposed to a mechanical stress or to predetermined external physical conditions in order to analyze the response thereto.

Various techniques and approaches may be applied for capturing the sequence of images depicting the derived human CM over an analysis period and/or determining one or more signals descriptive of the beating of the derived human CM during the analysis period on basis of the sequence of captured images. In the following, non-limiting examples and variations thereof for both capturing the images and determining the one or more signals are provided for the purpose of illustration.

The process of capturing a sequence of images depicting the derived human CM over the analysis period may comprise capturing the sequence of images by a video microscopy arrangement. Such arrangement may comprise a microscope of sufficient resolution having a digital video camera or a digital video camera module integrated therein. Alternatively, such an arrangement may comprise a dedicated microscope providing sufficient resolution and a digital camera or a digital camera module mounted thereon to capture the sequence of images through the microscope. The captured sequence of images is stored in a suitable storage medium, e.g. in a disk drive or in a storage apparatus of other suitable type for subsequent analysis.

The digital camera or the digital camera module is arranged to provide a sufficient frame rate in order to detect the beating motion of the derived human CM. The digital camera or the digital camera module may be provided as a dedicated digital video camera or a digital (still) camera capable of capturing images at the desired frame rate. As an example, the frame rate of 30 frames per second (fps) may be employed to ensure sufficient accuracy for the analysis of motion in the sequence of images. However, also lower fps rates, e.g. around 15 fps or even as low as 5 bps, may provide sufficient accuracy for the motion analysis. However, an advantage of frame rates of 15 fps or above is that they typically depict a single contraction/relaxation over a number of consecutive frames, thereby contributing to enable motion analysis at a sufficient accuracy. The sequence of images may be provided as the captured video sequence or the video sequence may be separated into a sequence separate (still) images.

Instead of a digital video camera or a digital video camera module, the images in the sequence of images may originate from a digital still camera of sufficient operating speed enabling provision of separate images at sufficiently short intervals, corresponding to the frame rates discussed hereinbefore. Consequently, the subsequent determination of the one or more parameters descriptive of the beating of the derived human CM may be based on the sequence of still images as such or on a video sequence composed on basis of the sequence of still images.

The captured images are preferably provided as monochrome images, e.g. as greyscale images. Pixels of the images may be represented e.g. 8-bit values, hence providing $2^8=256$ different levels of brightness. The resolution of the images as number of pixels may be selected e.g. such that the portion of captured images depicting the derived human CM of interest is at least 36×36 pixels, preferably around 50×50 pixels or more to provide a sufficient image resolution enabling accurate enough analysis of motion. While a different (e.g. higher) number of bits per pixel and a different (e.g. higher) image resolution may be employed, the exemplifying number of bits per pixel and exemplifying image resolution referred to hereinbefore provide a sufficient image quality that enables analysis of the motion at sufficient accuracy without using too much storage capacity.

The images may be directly captured as images of desired characteristics, e.g. as monochrome images at desired frame rate, with desired number of bits per pixel and/or at desired image resolution according the exemplifying image characteristics provided herein. Alternatively, the images may be captured in higher quality, e.g. at higher frame rate, in full colour, with higher number of bits per pixel and/or at higher image resolution and subsequently, i.e. before the analysis, converted into images of desired characteristics. While such avoidance of 'overprovisioning' of the image quality facilitates keeping the required storage capacity reasonable, it also serves to keep the computational complexity of the analysis lower.

The video microscopy arrangement is preferably positioned to face a cell culture hosting the one or more derived human CMs as a fixed arrangement, hence depicting a given derived human CM in the same region in each image of the sequence of images.

As briefly described hereinbefore, the analysis of images of the sequence of captured images over the analysis period comprises determining one or more parameters descriptive of the beating of the derived human CM during the analysis period or during a selected portion of the analysis period on basis of the of the sequence of captured images or a subset thereof corresponding to said selected portion of the analysis period. Examples of such parameters are provided hereinbefore.

Determination of the one or more parameters may comprise obtaining the sequence of images e.g. by reading the sequence from a storage medium, e.g. from a disk drive or from a storage apparatus of other suitable type, and using an appropriate image analysis method for determining motion within a region of interest in images of the sequence within the analysis period. In this regard, an exemplifying image analysis method that may be employed for motion analysis and its variations are described in detail hereinafter. Once determined, the one or more parameters descriptive of the beating of the derived human CM may be written on a storage medium for subsequent further analysis and/or provided for display e.g. on a display of a computer for immediate further analysis.

The analysis period preferably covers a plurality of cardiac cycles, typically tens or even hundreds of cardiac cycles in order to provide sufficient amount of data to reliably characterize and describe the beating of the derived human CM under study. Consequently, the temporal duration of the analysis period is dependent on the heartbeat of the derived human CM. A typical derived human CM exhibits heartbeat in the range from 20 to 90 beats per minute (bpm) and hence in order to have e.g. data covering at least 50 cardiac cycles the analysis period should cover a period of time approximately in the range from 0.5 to 1.5 minutes. The exemplifying ranges discussed herein are provided as non-limiting examples only and hence a derived human CM may exhibit heartbeat that is significantly lower than 20 bpm or significantly higher than 90 bpm and the duration of the analysis period should be determined accordingly in order to guarantee capturing a desired number of cardiac cycles for the analysis. The analysis period may be divided in temporally displaced time portions and a dedicated analysis to characterize the beating may be carried out for each time portion separately. This may be useful, for example, in characterization of an effect of a drug to the derived human CM over time.

Once the at least one signal descriptive of the beating of the derived human CM have been determined, in order to determine whether the at least signal exhibits characteristics meeting predetermined criteria indicative of the beating of a healthy human CM the at least one signal may be compared to respective reference signal(s) that are considered to indicate the beating behavior of a healthy human CM. As an example, this may involve visual inspection of the at least one signal, e.g. on basis of each of the at least signal provided as a curve indicative of the displacement of the respective sub-region of the derived human CM under study as a function of time on a computer display or on paper, in order to carry out comparison to one or more reference signals descriptive of beating of a healthy human CM.

As another example, the one or more parameters descriptive of the beating of the derived human CM that may be determined on basis of the at least one signal may compared to respective reference values that are considered to indicate the beating behavior of a healthy human CM. As an example in this regard, for a given parameter of the one or more parameters, such reference values may comprise the respective reference range indicative of the variation of the respective parameter value that is considered to reflect beating of a healthy human CM. Such a reference range may be defined e.g. as a minimum value of a parameter indicative of healthy beating behavior and/or as a maximum value of a parameter indicative of healthy beating behavior.

The reference values may be known values derived on basis of measurements of primary human CMs of reference persons known not to suffer any cardiac effects of problems. Alternatively, the reference values may be derived by applying plying the method 100 to a number of derived human CM originating from one or more reference persons known not to suffer any cardiac effects or problems.

Figure 4:
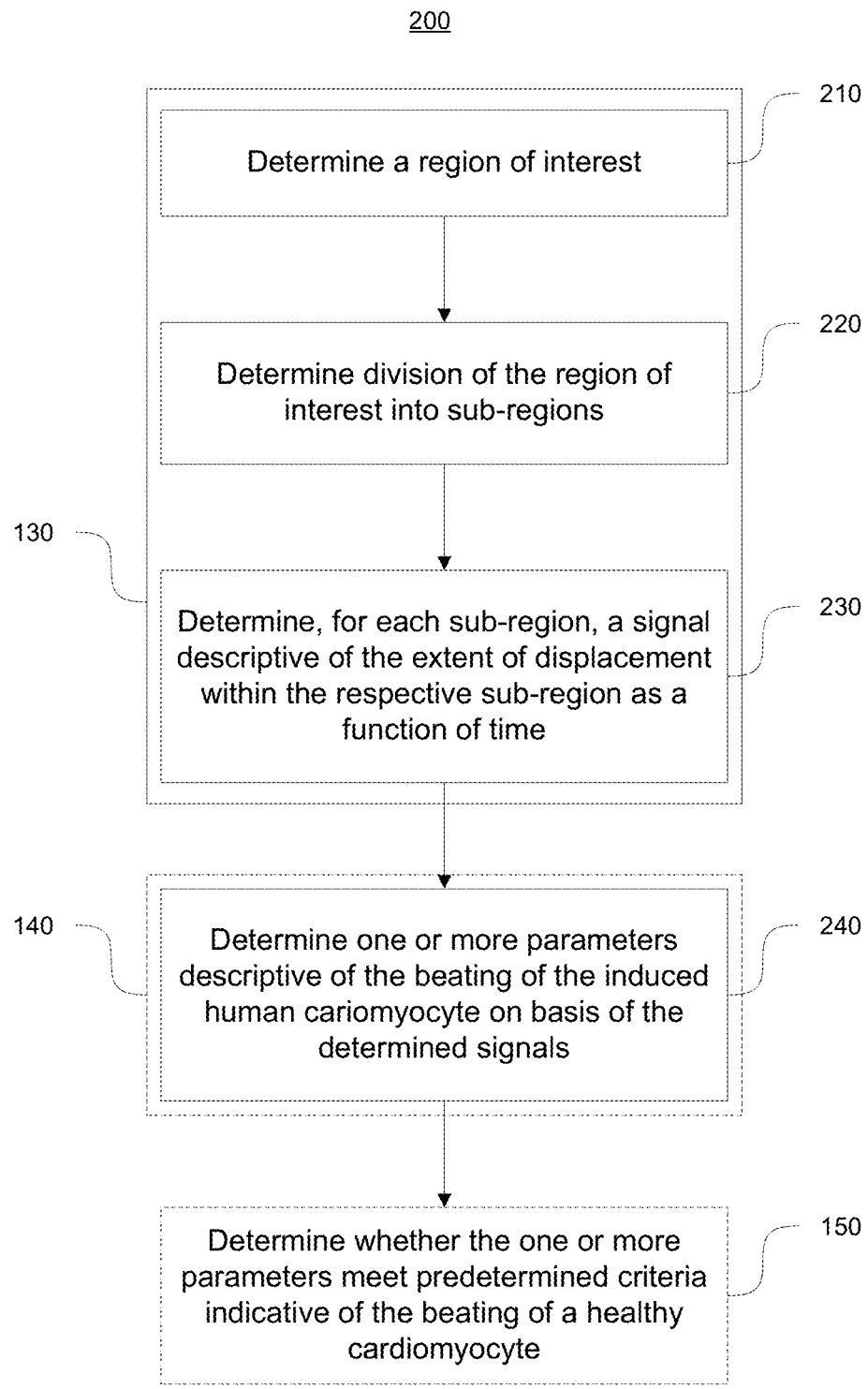
FIG. 4 illustrates a method in accordance with an exemplifying embodiment of the present invention.

In order to determine the at least signal descriptive of the beating of the derived human CM and, possibly, the one or more parameters descriptive of the beating of the derived human CM, the motion within the derived human CM as a function of time is determined. An exemplifying image analysis method 200, illustrated by a flowchart in FIG. 4, provides an example of an analysis technique suitable for analyzing the beating of the derived human CM in order to determine said one or more parameters. Since the images of the sequence of captured images depict a given derived human CM in the same region in each image of the sequence, it is sufficient to analyse movement within said region of images in order to analyse and characterize motion of the given derived human CM. Moreover, it may be sufficient to analyse and characterize the motion only within part of the region of the images depicting the given derived human CM. Therefore, only part(s) of said region exhibiting motion within the given derived human CM may be covered by the image analysis and characterization of motion. In the following, such region depicting the given derived human CM either full or in part is referred to as a region of interest.

Hence, the method 200 comprises determination of the region of interest, as indicated in block 210. The determination may comprise obtaining predetermined information indicating the location, e.g. the pixel positions, of the region of interest in images of the sequence of images. Alternatively, the determination of information indicating the location of the region of interest in images may be part of the method 200. The region of interest may be selected 'manually' on basis of visual inspection of images of the sequence of captured images. Alternatively, the region of interest may be selected or determined automatically, e.g. based on analysis of images and on observed motion within images of the sequence of captured images, as described by an example hereinafter.

The region of interest is further divided into two or more sub-regions, and the division into sub-regions may be either independent of the derived human CMs depicted in the region of interest or the division into sub-regions may be based at least in part on (pre-)analysis of the region of interest in images of the sequence of images, as described in more detail by examples hereinafter. In this regard, the method 200 may comprise determining the division of the region of interest into sub-regions, as indicated in block 220. As in case of determination of the region of interest, determining the division into sub-regions may comprise obtaining pre-determined information indicative of the locations, e.g. pixel positions, of the sub-regions in images of the sequence of images. Alternatively, determination of information indicative of location the sub-regions in images may be part of the method 200.

For each sub-region, at least one signal characterizing the extent of displacement or movement within the respective sub-region as a function of time is determined, as indicated in block 230. Consequently, there are two or more signals descriptive of the extent of displacement within the region of interest over time. Note that for brevity and clarity of description, at least one signal characterizing the extent of displacement or movement within the respective sub-region is described herein. However, such signal serves as an example of a signal characterizing the beating of the derived human CM and hence, additionally or alternatively, derivatives of such signals and/or suitable signals of other type may be employed. Example of such suitable signals include signals indicative of a position of a given portion of the respective sub-region over time, signals indicative of the speed of movement within the respective sub-region over time, signals indicative of the change in speed of movement within the respective sub-region over time, etc. Consequently, the one or more parameters descriptive of the beating of the induced human CM are optionally derived on basis of said two or more signals, as indicated in block 240. Once determined, the two or more signals or information indicative thereof may be written on a storage medium for subsequent further analysis and/or provided for display e.g. on a display of a computer for immediate further analysis. Alternatively or additionally, the one or more parameters descriptive of the beating of the derived human CM possibly determined on basis of the two or more signals or information indicative thereof may be written on the storage medium for subsequent use or further analysis.

Division into two or more sub-regions and derivation of the separate signals descriptive of the displacement or movement in these sub-regions is beneficial in that the derived human CM typically exhibits different motion in different areas of the CM, and therefore region-wise analysis of motion is likely to yield more accurate description of the beating of the derived human CM—in particular movement that may indicate unhealthy condition of the derived human CM. Moreover, typically even a single sub-region, and hence a portion of the derived human CM, exhibiting the beating behaviour different from that of a healthy CM serves as an indication of an unhealthy derived human CM.

Figure 5:
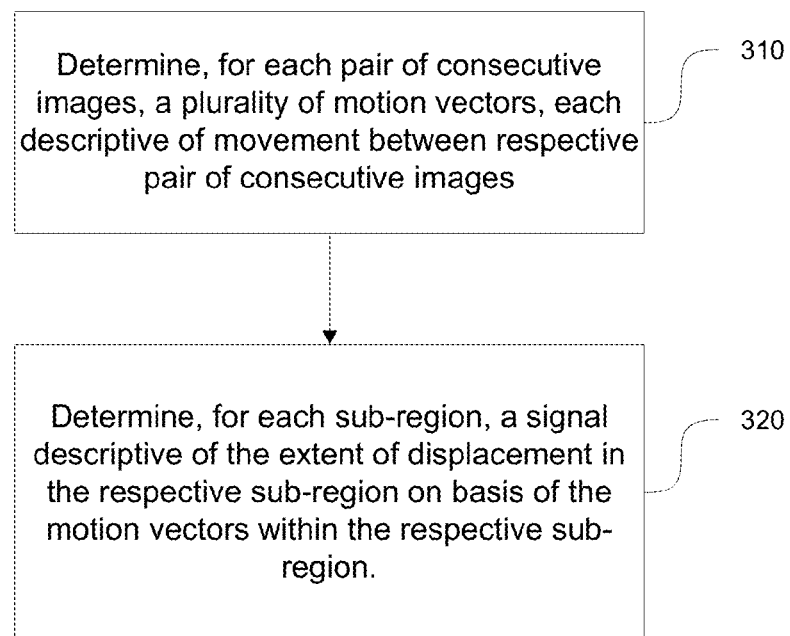
FIG. 5 illustrates a method in accordance with an exemplifying embodiment of the present invention.

While various approaches for determination of the at least signal descriptive of the extent of displacement of movement within a given sub-region as a function of time may be employed within the scope of the present invention, determination of said signal for a given sub-region may be carried out, for example, by using a motion analysis method 300 illustrated by a flowchart in FIG. 5. The method 300 comprises determining, for each pair of consecutive images of the sequence of captured images, a plurality of motion vectors, each motion vector descriptive of movement between respective pair of consecutive images, as indicated in block 310. The method 300 further comprises determining, for each sub-region of the region of interest, the respective signal descriptive of the extent of displacement therein on basis of the motion vectors of the plurality of motion vectors that are within the respective sub-region, as indicated in block 320.

Figure 6A:
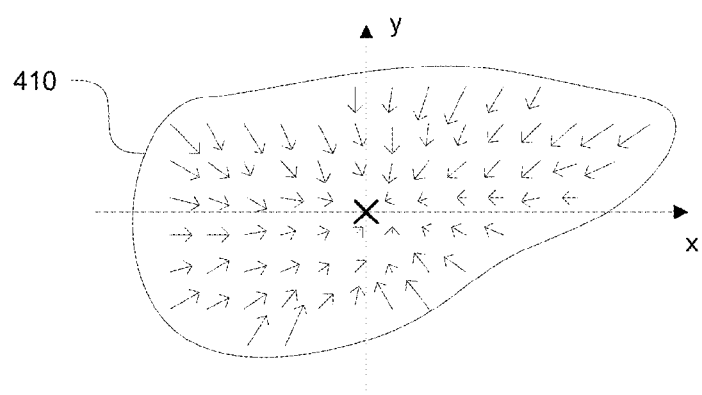
FIG. 6a schematically illustrates a plurality of motion vectors within a region of interest depicting a derived human CM.
Figure 6B:
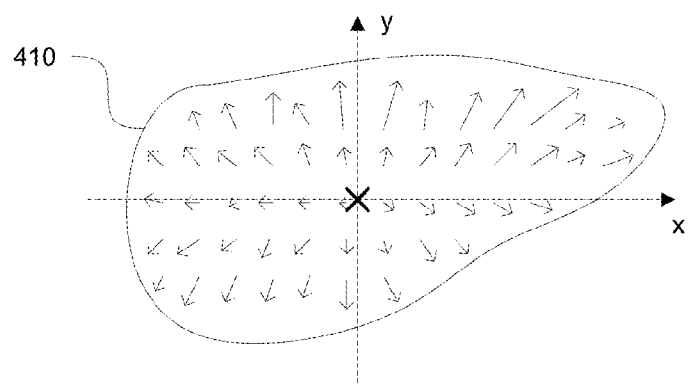
FIG. 6b schematically illustrates a plurality of motion vectors within a region of interest depicting a derived human CM.

Hence, each of the plurality of motion vectors is descriptive of the direction and extent of movement between a pair of consecutive images within the region of interest in the images. Consequently, the plurality of motion vectors represents the motion field between a given pair of consecutive images within the region of interest. The number and density of motion vectors within said region may be selected according to size of the region, according to desired granularity of the motion estimation and/or according to available processing power. The motion within the derived human CM, and hence within the region of interest, is typically either contractile movement or relaxation movement. Contractile movement is motion having its direction towards a focus point of motion, whereas the relaxation movement is motion away from the focus point of motion. In this regard, FIG. 6a schematically illustrates a plurality of motion vectors, shown as arrows, indicating contractile movement towards the (approximate) focus point of motion, indicated as a cross, within the region of interest 410. Along similar lines, FIG. 6b schematically illustrates a plurality of motion vectors indicating relaxation movement away from the focus point of motion within the region of interest 410. FIGS. 6a and 6b further illustrate x and y axes that are referred to in the following example regarding determination of the motion vectors. Note that for clarity of illustration FIGS. 6a and 6b do not explicitly show the derived human CM, but as described hereinbefore, the area of interest 410 covers either the derived human CM as a whole or a portion of the derived human CM.

As an example, a motion vector may be determined for a number of motion analysis blocks of N×N pixels in the region of interest. The motion analysis blocks may be adjacent blocks without overlap between the neighbouring blocks or, alternatively, neighbouring motion analysis blocks may employ partial overlap. As an example, motion analysis blocks of 16×16 pixels with 50% overlap both in direction of the x axis and in direction of the y axis is applied. For clarity and brevity of description, a motion analysis block may characterized by the pixel position (i, j) in the center of the motion analysis block, the motion analysis block hence extending from i−N/2 to i+N/2 in the direction of the x-axis and from j−N/2 to j+N/2 in the direction of the y-axis. Consequently, the motion vector for the motion analysis block at (i, j) may be determined as the displacement (dx, dy) that minimizes the quadratic difference between the motion analysis block at (i, j) in image $I_k$ and a block of corresponding size with its center at position (i+dx, j+dy) in image $I_{k+1}$. The process of determining the motion vectors is repeated for each pair of consecutive images $I_k$, $I^{k+1}$ within the analysis period. The process of determining the motion vectors within the region of interest described herein is provided as a non-limiting example only and variations of the described approach or approach(es) different from the one described herein may be employed without departing from the scope of the present invention.

Turning back to the selection of the region of interest, the 'manual' selection of the region of interest may comprise a user viewing one or more images of the sequence and using e.g. a user-interface of a computer to indicate the region interest in images to be subjected to analysis for determination of the at least one signal descriptive of the beating of the derived human CM of interest. The region of interest may be chosen as a region of a predetermined shape, such as a rectangle, a square, a circle or an ellipse depicting the derived human CM of interest or a portion thereof, or the region of interest may be chosen as region of arbitrary shape matching or essentially matching the shape of the derived human CM of interest or a portion of interest within the derived human CM.

The automatic selection of the region of interest may be carried out e.g. on basis of observed motion within the images of the sequence of captured images, in particular on basis of the motion vectors within the region of interest. The motion vectors determined as described hereinbefore may be employed as basis for the automatic selection or, alternatively, e.g. initial motion vectors determined on a coarser grid than the motion vectors described hereinbefore may be applied. Such initial motion vectors may be determined e.g. by applying motion analysis blocks of larger size without no overlap or with only a minor overlap with the adjacent blocks, and selecting the region of interest may comprise detecting one or more continuous clusters or areas where the (initial) motion vectors exhibit periodical motion throughout the analysis period, and selecting one of such clusters or areas as the region of interest. As an example, the cluster or area exhibiting highest average extent of motion may be selected as the area of interest. As another example, the automatic selection of the region of interest may be carried out by using image analysis to detect the outer line of a derived human CM in images of the sequence of images and selecting the region of interest accordingly. As a further example, alternatively or additionally, the automatic selection of the region of interest may be carried out on basis of image analysis to detect one or more organelles of the derived human CM within images of the sequence of images and selecting the region of interest accordingly.

Also the automatic selection of the region of interest may result in an area of a predetermined shape depicting the derived human CM of interest or a portion thereof or it may result in selection of an area of arbitrary shape matching or essentially matching the shape of the derived human CM of interest or a portion of interest within the derived human CM, as described hereinbefore in context of the 'manual' selection of the region of interest.

As already pointed out hereinbefore, the division of the region of interest into sub-regions may be either independent of the derived human CMs depicted in the region of interest or the division may be based at least in part on (pre-)analysis of the region of interest in images of the sequence of images. The division of the region interest into sub-regions implies assigning the motion analysis blocks within the area of interest into groups, each group corresponding to a given sub-region of the area of interest.

Figure 7:
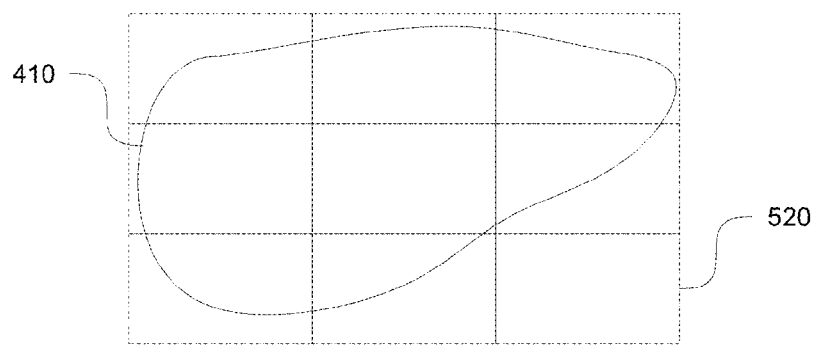
FIG. 7 schematically illustrates division of a region of interest into sub-regions regions on basis of a rectangular grid.

As a straightforward example of division into sub-regions without considering the characteristics of the derived human CM within the region of interest, the region of interest may be divided into a predetermined number of sub-regions on basis of a grid representing the shape and size of the sub-regions. As an example a rectangular grid divided into the predetermined number of rectangular sub-regions of equal or approximately equal size may be used. Since the region of interest being a rectangular region is a(n unlikely) special case, in such an approach the sub-regions at the edge of the region are typically non-rectangular. In this regard, the grid representing the shape and size of the predetermined number of rectangular sub-regions may be placed (approximately) in the center of the region of interest, and each of the actual sub-regions may be determined as the intersections of the respective sub-region of the grid and the region of interest. The predetermined number of rectangular sub-regions may be e.g. 9 or 16. As a variation of this straightforward example, the number of rectangular sub-regions may depend on size of the region of interest, such that increasing size of the region implies increasing number of sub-regions and/or the sub-regions of the grid may exhibit shape other than rectangular. FIG. 7 schematically illustrates division of the region of interest 410 in an image depicting the derived human CM into 9 sub-regions on basis of a rectangular grid 520 consisting of 9 rectangular sub-regions.

Figure 8:
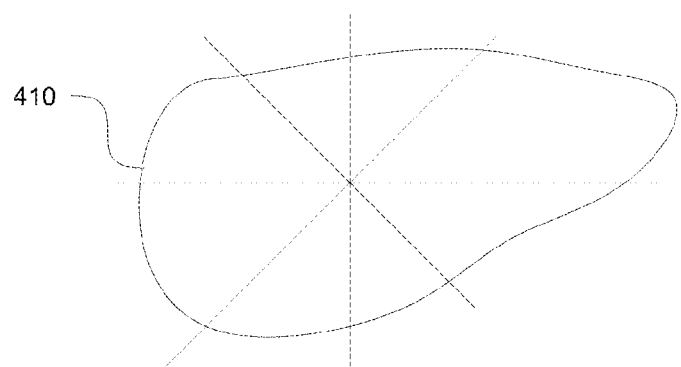
FIG. 8 schematically illustrates division of a region of interest into sub-regions based on circular sectors opening from a focus point of motion.

An example of a division into sub-regions that is at least in part based on (pre-)analysis of the region of interest in images, the division into sub-regions may comprise determination of the sub-regions as intersections of sectors of a conceptual circle of large/infinite radius having its focus in the focus point of the motion of the derived human CM with the region of interest and the region of interest. As an example, eight sectors of equal width may be employed, with each sector covering a sector of 45 degrees from the focus point of the motion, each sector truncated by the (conceptual) line determining the outer edge of the respective region of interest. The focus point of the motion may be determined by visual inspection (by a user) or e.g. on basis of the motion vectors and/or the initial motion vectors described hereinbefore—e.g. as the approximate point where the contracting movement indicated by the motion vectors and/or the initial motion vectors within the region of interest appears to converge. As a variation of this example, instead of determining or estimating the focus point of the motion on basis of the observed motion, the focus point of motion may be approximated e.g. as the center of mass of the derived human CM. An example of dividing the region of interest into sub-regions along these lines is provided in FIG. 8, which schematically illustrates the dashed lines dividing of the region of interest 410 into eight sectors of equal width in accordance with the example described hereinbefore.

Figure 9:
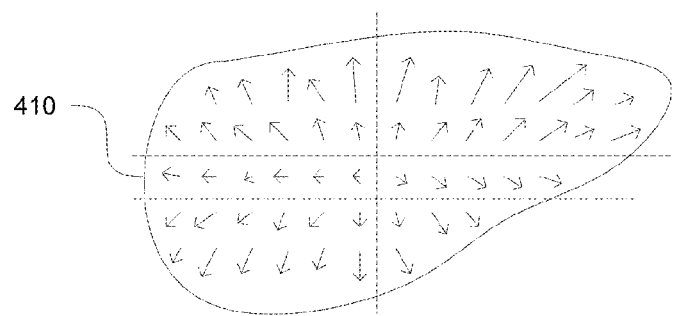
FIG. 9 schematically illustrates division of a region of interest into sub-regions on bases of observed movement within the region of interest.

As another example of division into sub-regions that is at least in part based on (pre-)analysis of the region of interest in images, the region of interest may be divided into sub-regions on basis of the motion vectors determined thereto. In particular, a preliminary analysis of the motion vectors over the analysis period or a portion thereof may be carried out in order to determine one or more continuous areas or clusters of motion vectors exhibiting motion of similar type, e.g. motion in the same or essentially the same direction and/or motion exhibiting similar or essentially similar extent, within the area of interest. Consequently, each of the one or more continuous areas or clusters is considered as one of the sub-regions. Such an approach may result in a situation where some portions of the region of interest are not assigned to any of the one or more areas or clusters and, consequently, such non-clustered portions may either be excluded from the motion analysis or they may form one or more further sub-regions. An example in this regard is provided in FIG. 9 schematically illustrating the region of interest 410 being divided by the dashed lines into six sub-regions, each of the six sub-regions exhibiting (relaxation) motion in a direction that is characteristics of the respective sub-region and which is different from that of the other sub-regions. As a variation of the example according to FIG. 9, alternatively or additionally, the division to sub-regions may consider the temporal alignment of the motion within the area of interest, e.g. by further dividing a sub-region determined on basis of motion in similar direction to two sub-regions where in one sub-region the state of (full) relaxation is relatively short and where the relaxation motion is slow but exhibits relatively static though the relaxation and where in the other sub-region the derived human CM stays in (fully) relaxed state for a prolonged period but exhibits relatively rapid relaxation motion.

Returning to the two or more signals descriptive of the extent of displacement or movement within the respective sub-region as a function of time, said two or more signals may be determined on basis of the motion vectors within the respective sub-region. As an example, for a given pair of consecutive images, a motion component corresponding to a given sub-region may be determined and computed as a sum of the motion vectors within the given sub-region. Such a motion component is determined and computed for each pair of consecutive images with the analysis period, and the signal corresponding to the given sub-region may be determined as concatenation of said motion components. Instead of the sum, e.g. the average or a weighted sum of the motion vectors may be used as basis for determination of the respective motion component.

Determining the two or more signals descriptive of the extent of displacement or movement with a given sub-region as a function of time may comprise determining the extent of displacement or motion with respect to a first reference axis. In such an approach the determination may comprise computing, for motion vectors of each pair of consecutive images, motion vector components descriptive of the motion along the first reference axis e.g. as dot product between a motion vector and the first reference axis. The motion component descriptive of the motion in a given sub-region for a given pair of consecutive images in direction of the first reference axis may be determined e.g. as the sum or as the average of said computed motion vector components within the respective sub-region, and the signal descriptive of the extent of displacement or motion along the first reference axis in the respective sub-region as a function of time may be determined as concatenation of said motion components. Consequently, a single signal descriptive of the motion along the first reference axis is determined for each sub-region. The first reference axis may be e.g. the x axis or the y axis.

In addition to determining for each sub-region a (first) signal descriptive of the extent of displacement or movement along the first reference axis, also a second signal descriptive of the extent of displacement or movement along a second reference axis as a function of time may be determined. In particular, the second reference axis has a direction different from that of the first reference axis. In such an approach the determination of the signals may hence additionally comprise computing, for motion vectors of each pair of consecutive images, motion vector components descriptive of the motion along the second reference axis e.g. as dot product between a motion vector and the second reference axis. The motion component descriptive of the motion in a given sub-region for a given pair of consecutive images in direction of the second reference axis may be determined e.g. as the sum or as the average of said computed motion vector components within the respective sub-region, and the signal descriptive of the extent of displacement or motion along the second reference axis in the respective sub-region as a function of time may be determined as concatenation of said motion components. Consequently, also a second signal descriptive of the motion along the second reference axis is determined for each sub-region. The first reference axis may be the x axis and the second reference axis may be the y axis.

Figure 10:
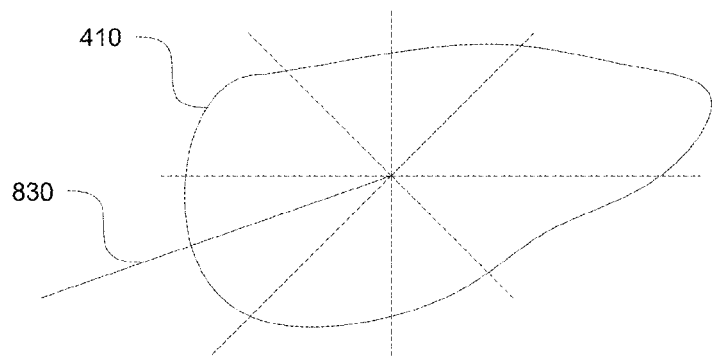
FIG. 10 schematically illustrates a reference axis for motion analysis within a sub-region provided as a radial axis with respect to a focus point of motion.

While the description hereinbefore assumed one or two fixed reference axes that are the same over all sub-regions, it is also possible to employ reference axis or axes that are chosen in dependence of the sub-region. For example in context of the example employing sub-regions determined as intersections of sectors of a conceptual circle described hereinbefore in context of FIG. 8, for each sector-based sub-region the center line of the respective sector may be employed as the first reference axis. An example in this regard is provided in FIG. 10, illustrating such a center line 830 for a single sub-region of the region of interest 410. Instead of the center line of the sub-region, e.g. any axis extending from the focus point of the motion towards outer edge of the region of interest with the respective sub-region may be employed as the first reference axis. Consequently, the first reference axis forms a radial axis with respect to the focus point of the motion of the derived human CM and the motion along the first reference axis serves to indicate motion in radial direction.

In case also a second signal descriptive of the extent of displacement or movement in direction of the second reference axis is employed, for each sub-region a normal of the radial axis may be employed as the respective second reference axis. Consequently, the second reference axis forms a tangential axis with respect to the focus point of the motion of the derived human CM and the motion along the second reference axis serves to indicate motion in tangential direction. While in such an arrangement of sub-regions the radial direction can be expected to capture a major component of the overall motion within the respective sub-region, the tangential direction may provide useful additional information descriptive of motion exhibiting direction significantly different from the radial axis.

Figure 11:
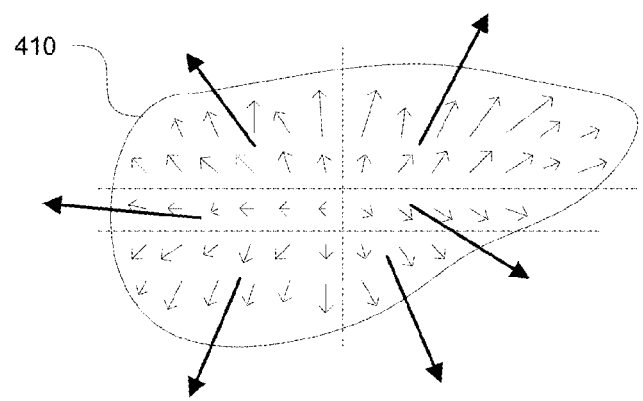
FIG. 11 schematically illustrates a reference axis for motion analysis within a sub-region determined on basis of observed motion therein.

As a further example of axis or axes selected in dependence of a sub-region, the first reference axis for a given sub-region may represent the observed main direction of movement within the given sub-region. As an example, in case the region of interest is divided into sub-regions on basis of the motion vectors determined thereto, as described hereinbefore in context of FIG. 9, the first reference axis of a given sub-region may be e.g. the average direction of the motion vectors within the given sub-region over the analysis period, thereby making the selection of the first reference axis dependent on the characteristics of the motion of the derived human CM under study. An example in this regard is provided in FIG. 11, schematically illustrating an example of the first reference axes suitable for the example of division in the sub-regions described hereinbefore in context of FIG. 9. In case also a second signal descriptive of the extent of displacement or movement in direction of the second reference axis is employed, for each sub-region a normal of the first reference axis may be employed as the respective second reference axis in order to effectively capture motion that may be different in terms of direction in comparison to the 'main' movement that is used as basis for determining the first reference axis.

Regardless of the approach employed for dividing the region of interest in sub-regions and/or the number and direction of the reference axes employed in determination of the two or more signal descriptive of the extent of displacement or motion, motion vectors or motion vector components that are involved in determination of said two or more signals may be pre-processed before determination of the respective motion components.

As an example in this regard, a median filter may be applied to time series of motion vector components along the first and/or second reference axis corresponding to a given sub-region of the region of interest in order to smooth the motion field before combining the motion vector components within the given sub-region into motion components representing the extent of motion between pairs of consecutive images in the given sub-region. As another example, a statistical analysis of the motion vector components along the first and/or second axis within a given sub-region may be applied, and for a given pair of consecutive images motion vector components exhibiting (extent of) motion outside a given range may be excluded from consideration in the process of combining the motion vector components into a motion component corresponding the given pair of consecutive images. The given range may include, for example, the motion vector components within the range $M_{avg} - f \times M_{std} \ldots M_{avg} + f \times M_{std}$, where $M_{avg}$ denotes the average value of the motion vector components for the given pair of consecutive images within the given sub-region, $M_{std}$ denotes the standard deviation of the motion vector components for the given pair of consecutive images within the given sub-region and f is a scaling factor having a desired value, e.g. value f=2.5 may be used.

A single signal of the two or more signal characterizing descriptive of the extent of displacement or movement within the respective sub-region of the region of interest may be considered in evaluation of the beating of the derived human CM of interest. Consequently, the one or more parameters may be derived on basis of said single signal. The single signal may be selected, for example, by a user on basis of the visual inspection of the signal reproduced e.g. as a curve indicative of the displacement of the respective sub-region of the derived human CM under study as a function of time on a computer display or on paper. The selection criterion aims to select a signal that exhibits characteristics that are considered indicative of suitability of the signal to represent the characteristics of the beating of the derived human CM and hence would also be suitable for determination of the one or more parameters. Such selection may comprise selecting a signal that appears to exhibit a minimum amount of noise and disturbances, selecting a signal that appears to be prominently different from the other signals, selecting a signal that appears to exhibit largest extent of displacement, etc. Instead of the user selecting the single signal, intermediate parameters characterizing the signal in such a way that suitability of the signal for characterizing the beating behaviour may be computed. Consequently, the single signal may be selected on basis of the intermediate parameters. As an example, the intermediate parameters may comprise power spectrum of the two or more signals over the analysis period or a portion thereof, and the single signal may be selected e.g. as the signal of the two or more signals that exhibits highest average power or highest variation in power over time.

Alternatively, instead of relying only on a single signal, two or more of the signals descriptive of the extent of displacement or movement within the respective sub-region of the region of interest may be considered in evaluation of the beating of the derived human CM of interest. Consequently, separate sets of one or more parameters may be derived on basis two or more of the two or more signals descriptive of the extent of displacement or movement within the respective sub-region of the region of interest. As an example, a predetermined number of signals, e.g. three signals, may be selected for further analysis, e.g. as subjects to determination of the one or more parameters descriptive of the beating. The selection may follow the same principle as selection of the single signal with the similar criteria applied in order to select a predetermined number of signals that most prominently exhibit characteristics considered to indicate suitability of the signal to represent the characteristics of the beating of the derived human CM.

As a further example, instead of using a single signal or a plurality of signals as such to represent the characteristics of the beating of the derived human CM and possibly for subsequent determination of the one or more parameters, two or more of the two or more signals may be combined into a combined signal, which will be used as a signal descriptive of the beating of the derived human CM of interest. Consequently, the one or more parameters may be determined on basis of the combined signal. The combination may involve, for example, summing the signals or averaging the signals. The signals of the two or more signals to be used as the basis for the combined signal may be e.g. selected in a manner described hereinbefore for selecting a predetermined number of signals or all determined signals may be combined into the combined signal.

Although described hereinbefore for a single derived human CM, the methods 100, 200 and 300 may be employed to analyse a plurality of derived human CMs in parallel. In particular, this may involve obtaining a plurality of derived human CMs, capturing a sequence of images depicting the plurality of derived human CMs, determining each or some of the CMs as regions of interest with automated or manual methods, determining the at least one signal descriptive of the beating of the respective derived human CM during an analysis period on basis of the sequence of captured images for each derived human CM of the plurality of derived human CM separately, and possibly determining the one or more parameters descriptive of the beating of the derived human CM on basis of the respective at least one signal for each derived human CM of the plurality of derived human CM separately.

The possible determination whether the one or parameters descriptive of the beating of a given induced derived human CM of the plurality of induced derived human CMs meet the predetermined criteria indicative of a healthy human CM may be carried out separately for each of the plurality of induced derived human CMs. This provides an opportunity to separate subgroups of human CMs with distinctive mechanical behaviour based on one or plurality of the parameters. Consequently, e.g. in case the plurality of the induced derived human CMs originate from a single person, e.g. the percentage of the induced derived human CMs found to indicate healthy (or unhealthy) behaviour may be considered as an indication of the condition of this person e.g. for the assessment of the seriousness of the impact of his/her genotype on his/her cardiac functions.

As an example in this regard, the analysis and characterization of a plurality of derived human CMs enables identifying two or more subgroups within the plurality of derived human CMs based on the observed beating characteristics. The classification into subgroups may serve e.g. to divide the derived human CMs into subgroups of different beating characteristics and/or into subgroups of different phenotypes e.g. providing the patient specific subgroups of diseased and healthy CMs. Consequently, only a single CM subgroup or a plurality of the CM subgroups may be selected for subsequent further analysis, e.g. for testing the reaction to exposure to a substance of interest, e.g. to a drug, to a molecule or to a toxin. Alternatively, the division into subgroups may serve to support subsequent diagnosis e.g. by indicating the extent or severity of a condition indicated by the analysis of the plurality of derived human CMs. Consequently, a single CM subgroup or a plurality of the CM subgroups with selected conditions of the individual can be used to seek for an optimal substance, e.g. a drug or a molecule, that can improve the condition of the subgroup of CMs providing possible cure or improvement of the condition of the individual.

The methods 100, 200 and 300 described hereinbefore and variations thereof may be applied, for example to identify or to support identification of a derived human CM with a genetic alteration or mutation. Further non-limiting examples of the applicability of the methods 100, 200 and 300 and variations thereof include identifying or supporting identification of a diseased derived human CM, identifying or supporting identification of a normally beating derived human CM and/or identifying or supporting identification of a corrective and/or an adverse effect of a substance of interest on a derived human CM.

Figure 12:
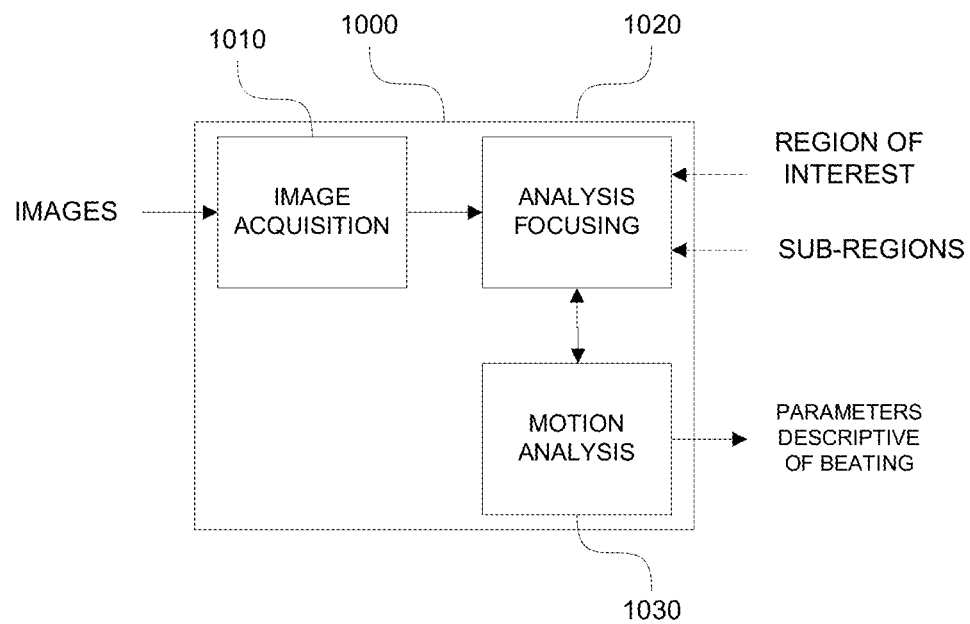
FIG. 12 schematically illustrates an image analyzer in accordance with an exemplifying embodiment of the invention.

FIG. 12 schematically illustrates an image analyzer 1000 for analyzing the beating of the derived human CM on basis of the sequence of captured images. The image analyzer 1000 comprises an image acquisition portion 1010 for obtaining the sequence of captured images depicting the derived human CM, an analysis focusing portion 1020 for obtaining information indicative of the region of interest within images of the sequence of captured images and a motion analysis portion 1030 for determining at least one signal descriptive of the beating of the derived human CM. The image analyzer 1000 may be implemented by software means, by hardware means or by combination of software and hardware means and provided e.g. as an image analysis apparatus or a portion of such an apparatus.

The image acquisition portion 1010 is configured to obtain the sequence of captured images depicting the derived human CM under study over an analysis period. Obtaining the images may comprise reading a pre-captured sequence of images from a memory or a storage device provided in the image analyzer 1000 or in a separate entity accessible by the image acquisition portion 1010. Alternatively, obtaining the images may comprise the image acquisition portion 1010 control operation of a video microscopy arrangement described hereinbefore and storing the images acquired therefrom into the memory or the storage device provided in the image analyzer 1000 or in a separate entity accessible by the image acquisition portion 1010 and, subsequently, obtaining the images by reading from the memory or storage apparatus as described hereinbefore in context of the method 100.

The analysis focusing portion 1020 is configured to obtain information indicative of the region in images of the sequence of images depicting the derived human CM of interest, referred to as the region of interest. The analysis focusing portion 1020 is further configured to obtain information indicative of two or more sub-regions within the region of interest. The analysis focusing portion 1020 may be configured to obtain information regarding the region of interest and the sub-regions of the region of interest as described hereinbefore in context of methods 200 and 300. Hence, the analysis focusing portion 1020 may be configured to obtain indication of the region of interest either on basis of user input or on basis of observed motion in images of the sequence of captured images, as described by the detailed examples provided hereinbefore. Moreover, the analysis focusing portion 1020 may be configured to obtain information regarding the sub-regions of the region of interest either on basis of user input or based at least in part on (pre-)analysis of motion within the region of interest in images of the sequence, as described by the detailed examples provided hereinbefore. The motion analysis that may be used as basis for selection of the region of interest and/or the sub-regions may be provided by the motion analysis portion 1030.

The motion analysis portion 1030 is configured to determine two or more signals characterizing the displacement within the region of interest, each of the two or more signals characterizing the extent of displacement within a respective sub-region of said region as a function of time. The motion analysis portion 1030 may be optionally further configured to determine one or more parameters descriptive of the beating of the derived human CM on basis of said two or more signals. The motion analysis portion 1030 may be configured to provide the one or more parameters descriptive of the beating of the derived human CM and/or the two or more signals descriptive the extent of displacement within a respective sub-region of said region as a function of time for storage in a memory or a storage device in the image analyzer 1000 or in a separate entity accessible by the motion analysis portion 1030 for subsequent further analysis and/or to a display comprised in the image analyzer 1000 or connected thereto to be displayed for immediate further analysis.

In this regard, the motion analysis portion 1030 may be configured to carry out, in conjunction with the analysis focusing portion 1020, the method 200 described in detail hereinbefore. Moreover, the motion analysis portion 1030 may be further configured to carry out the method 300 described in detail hereinbefore.

As an example in this regard, the motion analysis portion 1030 may be configured to obtain information regarding the region of interest within the images and the sub-regions thereof from the analysis focusing portion 1020. Moreover, the motion analysis portion 1030 may be configured to determine the two or more signals by determining, for each pair of consecutive images of the sequence within the analysis period, a plurality of motion vectors, each motion vector descriptive of movement between respective pair of consecutive images within the region of interest, and by determining, for each sub-region, said signal characterizing the extent of displacement within the respective sub-region on basis of a subset of the plurality of motion vectors, which subset comprises the motion vectors within the respective sub-region. Further in this regard, determination of the plurality of motion vectors may comprise determining, for each motion vector, a first motion component descriptive of movement along a first axis and a second motion component descriptive of movement along a second axis, wherein for each sub-region a first signal descriptive of movement along the first axis is determined on basis of motion components descriptive of movement along the first axis and a second signal descriptive of movement along the second axis is determined on basis of motion components descriptive of movement along the second axis. Alternatively, only the motion components descriptive of movement along the first axis may be determined and, consequently, only the (first) signal descriptive of movement along the first axis is determined on basis of the motion components descriptive of movement along the first axis. Further details and variations regarding determination of the motion vectors, the axes employed for the determination of the motion components and different sub-region allocations are provided hereinbefore in context of description of the methods 100, 200 and 300.

Along the lines described hereinbefore for the methods 100, 200 and 300, also the image analyzer 1000 may be employed to analyse a plurality of derived human CMs in parallel to enable e.g. identifying two or more subgroups within the plurality of derived human CMs based on the observed beating characteristics. Moreover, along the lines described hereinbefore for the methods 100, 200 and 300, also the image analyzer 1000 and/or variations thereof may be applied or used, for example to identify or to support identification of a derived human CM with a genetic alteration or mutation. Further non-limiting examples of the application or use of the image analyzer 1000 include using the image analyzer 1000 and/or a variation thereof to identify or to support identification of a diseased derived human CM, to identify or to support identification of a normally beating derived human CM and/or to identify or to support identification of a corrective and/or an adverse effect of a substance of interest on a derived human CM.

The operations, procedures and/or functions assigned to the structural units of the image analyzer 1000, e.g. to the image acquisition portion 1010, to the analysis focusing portion 1020 and to the motion analysis portion 1030, may be divided between these portions in a different manner. Moreover, the image analyzer 1000 may comprise further portions or units that may be configured to perform some of the operations, procedures and/or functions assigned to the image acquisition portion 1010, to the analysis focusing portion 1020 and to the motion analysis portion 1030 in the description hereinbefore.

On the other hand, the operations, procedures and/or functions assigned to the image acquisition portion 1010, to the analysis focusing portion 1020 and to the motion analysis portion 1030 may be assigned to a single portion or to a single processing unit within the controller 220. In particular, the image analyzer 1000 may be provided as an image analysis apparatus for analyzing the beating of a derived human CM on basis of a sequence of captured images, said apparatus comprising means for obtaining the sequence of images depicting the derived human CM over an analysis period, means for obtain information indicative of the region of the images depicting the derived human CM, means for obtaining information indicative of two or more sub-regions within said region, and means for determining two or more signals characterizing the displacement within said region of the images depicting the derived human CM, each signal characterizing the extent of displacement within a respective sub-region of said region as a function of time. Moreover, the image analysis apparatus may further comprise means for determining one or more parameters descriptive of the beating of the derived human CM on basis of said two or more signals.

Figure 13:
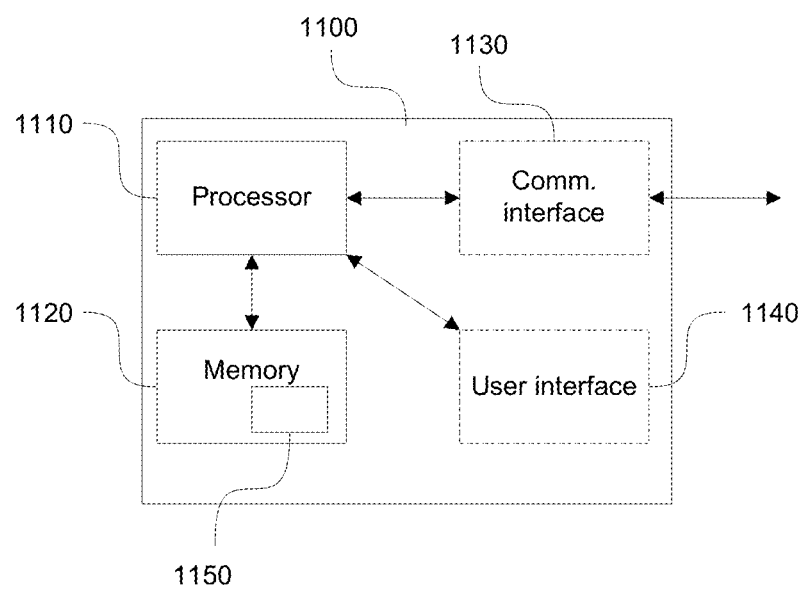
FIG. 13 schematically illustrates an apparatus in accordance with an exemplifying embodiment of the invention.

As a non-limiting further example, FIG. 13 schematically illustrates an exemplifying apparatus 1100 that may be employed for embodying the image analyzer 1000. The apparatus 1100 comprises a processor 1110 and a memory 1120, the processor 1110 being configured to read from and write to the memory 1120. The apparatus 1100 may further comprise a communication interface 1130, such as a network card or a network adapter enabling wireless or wired communication with one or more another apparatuses. The apparatus 1100 may further comprise a user interface 1140 for providing data, commands and/or other input to the processor 1110 and/or for receiving data or other output from the processor 1110, the user interface 1140 comprising for example one or more of a display, one or more keys, a keyboard, a mouse or a respective pointing device, a touchscreen, etc. The apparatus 1100 may comprise further components not illustrated in the example of FIG. 13.

Although the processor 1110 is presented in the example of FIG. 13 as a single component, the processor 1110 may be implemented as one or more separate components. Although the memory 1120 is illustrated as single component, the memory 1120 may be implemented as one or more separate components, some or all of which may be integrated/removable and/or may provide permanent/semi-permanent/dynamic/cached storage.

The apparatus 1100 may be embodied as a special-purpose or as a general purpose device with a sufficient processing capacity. Alternatively, the apparatus 1100 may be embodied as an apparatus dedicated for operating as the image analyzer 1000 described hereinbefore.

The memory 1120 may store a computer program 1150 comprising computer-executable instructions that control the operation of the apparatus 1100 when loaded into the processor 1110 and executed by the processor 1110. As an example, the computer program 1150 may include one or more sequences of one or more instructions. The computer program 1150 may be provided as a computer program code. The processor 1110 is able to load and execute the computer program 1150 by reading the one or more sequences of one or more instructions included therein from the memory 1120. The one or more sequences of one or more instructions may be configured to, when executed by one or more processors, cause an apparatus, for example the apparatus 1100, to implement the operations, procedures and/or functions described hereinbefore in context of the image analyzer 1000.

Hence, the apparatus 1100 may comprise at least one processor 1110 and at least one memory 1120 including computer program code for one or more programs, the at least one memory 1120 and the computer program code configured to, with the at least one processor 1110, cause the apparatus 1100 to perform the operations, procedures and/or functions described hereinbefore in context of the image analyzer 1000.

The computer program 1150 may be provided independently of the apparatus, and the computer program 1150 may be provided at the apparatus 1100 via any suitable delivery mechanism. As an example, the delivery mechanism may comprise at least one computer readable non-transitory medium having program code stored thereon, the program code which when executed by an apparatus cause the apparatus at least implement processing to carry out the operations, procedures and/or functions described hereinbefore in context of the image analyzer 1000. The delivery mechanism may be for example a computer readable storage medium, a computer program product, a memory device a record medium such as a CD-ROM, a DVD, a corresponding optical media, an article of manufacture that tangibly embodies the computer program 1150, etc. As a further example, the delivery mechanism may be a signal configured to reliably transfer the computer program 850.

Reference to a processor should not be understood to encompass only programmable processors, but also dedicated circuits such as field-programmable gate arrays (FPGA), application specific circuits (ASIC), signal processors, etc. Features described in the preceding description may be used in combinations other than the combinations explicitly described. Although functions have been described with reference to certain features, those functions may be performable by other features whether described or not. Although features have been described with reference to certain embodiments, those features may also be present in other embodiments whether described or not.

The invention claimed is:

1. A method for analyzing the beating of a derived human cardiomyocyte, the method comprising
    obtaining the derived human cardiomyocyte,
    capturing a sequence of images depicting the derived human cardiomyocyte over an analysis period, and
    determining at least one signal descriptive of the beating of the derived human cardiomyocyte during the analysis period on basis of the sequence of captured images, comprising determining two or more signals characterizing the displacement within a region of the images depicting the derived human cardiomyocyte, each signal characterizing the extent of displacement within a respective sub-region of said region as a function of time,
    wherein said sub-regions are intersections of said region and sectors of a circle having its center in the focus point of the motion of the derived human cardiomyocyte, and
    wherein, for a given sub-region, said two or more signals characterize the extent of displacement along a first axis that is a radial axis with respect to the focus point of the motion within the respective sector and the extent of displacement along a second axis that is a normal of the first axis.

2. The method according to claim 1, further comprising determining one or more parameters descriptive of the beating of the derived human cardiomyocyte on basis of the at least one signal.

3. The method according to claim 2, further comprising determining whether the one or more parameters meet predetermined criteria indicative of the beating of a healthy human cardiomyocyte.

4. The method according to claim 1, wherein said obtaining comprises deriving the human cardiomyocyte on basis of a source cell.

5. The method according to claim 4, wherein said deriving comprises differentiating the derived human cardiomyocyte on basis of an induced pluripotent stem cell.

6. The method according to claim 1, wherein determining said two or more signals comprises
    determining, for each pair of consecutive images within the analysis period, a plurality of motion vectors, each motion vector descriptive of movement between respective pair of consecutive images within said region of the images depicting the derived human cardiomyocyte, and
    determining, for each sub-region, said signal characterizing the extent of displacement within the respective sub-region on basis of the motion vectors within the respective sub-region.

7. The method according to claim 6, wherein determining the plurality of motion vectors comprises
    determining, for each motion vector, a first motion component descriptive of movement along the first axis and a second motion component descriptive of movement along the second axis, and
    wherein for each sub-region a first signal descriptive of movement along the first axis is determined on basis of motion components descriptive of movement along the first axis and a second signal descriptive of movement along the second axis is determined on basis of motion components descriptive of movement along the second axis.

8. The method according to claim 2, wherein said one or more parameters descriptive of the beating comprise one or more of the following:
    duration of a period of relaxation of the derived human CM in relation to the beating rate of the derived human CM,
    duration of the period of the derived human CM being in fully contracted state in relation to the beating rate of the derived human CM, and
    duration of the period of disrupted relaxation movement of the derived human CM in relation to the beating rate of the derived human CM.

9. The method according to claim 1,
    wherein the method is applied to a plurality of derived human cardiomyocytes in parallel, and
    wherein the method further comprises classifying said plurality of derived human cardiomyocytes into two or more subgroups in accordance with observed beating characteristics of said plurality of derived human cardiomyocytes.

10. The method according to claim 1, wherein the method is applied to identify one or more of the following:
    a derived human cardiomyocyte with a genetic alteration or mutation,
    a corrective and/or an adverse effect of a substance of interest on a derived human cardiomyocyte,
    identification of a diseased derived human cardiomyocyte, and identification of a normally beating derived human cardiomyocyte.

11. An apparatus for analyzing the beating of a derived human cardiomyocyte on basis of a sequence of captured images, the apparatus comprising
- an image acquisition portion configured to obtain the sequence of images depicting the derived human cardiomyocyte over an analysis period,
- an analysis focusing portion configured to
- obtain information indicative of the region of the images depicting the derived human cardiomyocyte, and
- obtain information indicative of two or more sub-regions within said region, and
- an image analysis portion configured to determine two or more signals characterizing the displacement within said region of the images depicting the derived human cardiomyocyte, each signal characterizing the extent of displacement within a respective sub-region of said region as a function of time,
- wherein said sub-regions are intersections of said region and sectors of a circle having its center in the focus point of the motion of the derived human cardiomyocyte, and
- wherein, for a given sub-region, said two or more signals characterize the extent of displacement along a first axis that is a radial axis with respect to the focus point of the motion within the respective sector and the extent of displacement along a second axis that is a normal of the first axis.

12. The apparatus according to claim 11, wherein the image analysis portion is further configured to determine one or more parameters descriptive of the beating of the derived human cardiomyocyte on basis of said two or more signals.

13. The apparatus according to claim 11, wherein determining said two or more signals comprises
- determining, for each pair of consecutive images within the analysis period, a plurality of motion vectors, each motion vector descriptive of movement between respective pair of consecutive images within said region of the images depicting the derived human cardiomyocyte, and
- determining, for each sub-region, said signal characterizing the extent of displacement within the respective sub-region on basis of the motion vectors within the respective sub-region.

14. The apparatus according to claim 13,
- wherein determining the plurality of motion vectors comprises determining, for each motion vector, a first motion component descriptive of movement along the first axis and a second motion component descriptive of movement along the second axis, and
- wherein for each sub-region a first signal descriptive of movement along the first axis is determined on basis of motion components descriptive of movement along the first axis and a second signal descriptive of movement along the second axis is determined on basis of motion components descriptive of movement along the second axis.

15. An apparatus for analyzing the beating of a derived human cardiomyocyte on basis of a sequence of captured images, the apparatus comprising at least one processor and at least one memory including computer program code for one or more programs, the at least one memory and the computer program code configured to, with the at least one processor, cause the apparatus to perform at least the following:
- obtain the sequence of images depicting the derived human cardiomyocyte over an analysis period,
- obtain information indicative of the region of the images depicting the derived human cardiomyocyte,
- obtain information indicative of two or more sub-regions within said region, and
- determine two or more signals characterizing the displacement within said region of the images depicting the derived human cardiomyocyte, each signal characterizing the extent of displacement within a respective sub-region of said region as a function of time,
- wherein said sub-regions are intersections of said region and sectors of a circle having its center in the focus point of the motion of the derived human cardiomyocyte, and
- wherein, for a given sub-region, said two or more signals characterize the extent of displacement along a first axis that is a radial axis with respect to the focus point of the motion within the respective sector and the extent of displacement along a second axis that is a normal of the first axis.

16. The apparatus according to claim 15, wherein the at least one memory and the computer program code are further configured to, with the at least one processor, cause the apparatus to determine one or more parameters descriptive of the beating of the derived human cardiomyocyte on basis of said two or more signals.

17. A computer readable non-transitory medium having program code stored thereon, the program code, when executed by an apparatus, causes the apparatus to analyze the beating of a derived human cardiomyocyte on basis of a sequence of captured images, at least performing the following:
- obtain the sequence of images depicting the derived human cardiomyocyte over an analysis period,
- obtain information indicative of the region of the images depicting the derived human cardiomyocyte,
- obtain information indicative of two or more sub-regions within said region, and
- determine two or more signals characterizing the displacement within said region of the images depicting the derived human cardiomyocyte, each signal characterizing the extent of displacement within a respective sub-region of said region as a function of time,
- wherein said sub-regions are intersections of said region and sectors of a circle having its center in the focus point of the motion of the derived human cardiomyocyte, and
- wherein, for a given sub-region, said two or more signals characterize the extent of displacement along a first axis that is a radial axis with respect to the focus point of the motion within the respective sector and the extent of displacement along a second axis that is a normal of the first axis.

18. The computer readable non-transitory medium according to claim 17, further comprising instructions which, when executed by one or more processors, cause the apparatus to determine one or more parameters descriptive of the beating of the derived human cardiomyocyte on basis of said two or more signals.

* * * * *